United States Patent [19]

Gahn

[11] Patent Number: 5,091,656
[45] Date of Patent: Feb. 25, 1992

[54] FOOTSWITCH ASSEMBLY WITH ELECTRICALLY ENGAGED DETENTS

[75] Inventor: Gerald S. Gahn, Manchester, Mo.

[73] Assignee: Storz Instrument Company, St. Louis, Mo.

[21] Appl. No.: 428,355

[22] Filed: Oct. 27, 1989

[51] Int. Cl.$^5$ .............................................. G05G 5/03
[52] U.S. Cl. ................................. 307/119; 200/86.5
[58] Field of Search ............................ 200/86.5, 61.89; 307/119, 132 EA; 74/478, 512

[56] References Cited

U.S. PATENT DOCUMENTS

| | | | |
|---|---|---|---|
| 2,863,962 | 9/1955 | Letteney | 200/86.5 X |
| 3,613,608 | 10/1971 | Hinerfeld et al. | 112/2 |
| 3,983,344 | 9/1976 | Straihammer | 200/86.5 |
| 4,513,235 | 4/1985 | Acklam et al. | 318/685 |
| 4,516,063 | 5/1985 | Kaye et al. | 318/685 |
| 4,837,857 | 6/1989 | Scheller et al. | 455/617 |
| 4,983,901 | 1/1991 | Lehmer | 318/365 |

FOREIGN PATENT DOCUMENTS

657254 2/1963 Canada .............................. 200/86.5

Primary Examiner—A. D. Pellinen
Assistant Examiner—Fritz M. Fleming
Attorney, Agent, or Firm—Brooks & Kushman

[57] ABSTRACT

A footswitch apparatus for remotely controlling a surgical instrument. The footswitch apparatus preferably includes a base and a footpedal movably mounted to the base. The footpedal is movable within set upward and downward limits. In one mode of operation, the downward travel of the footpedal is resisted by different springs and different ranges of travel. The footpedal position is sensed and the operation of the surgical instrument is altered depending on which of the ranges the footpedal is in. This gives the operator constant tactile feedback as to which range of travel the footpedal is in. In addition, in a second mode of operation, the multiple springs are decoupled and only a single spring is experienced throughout the range of travel. This provides a flexibility so that the same footswitch apparatus can be used to operate a surgical instrument in a particular mode with linear control throughout the range of footpedal travel.

15 Claims, 9 Drawing Sheets

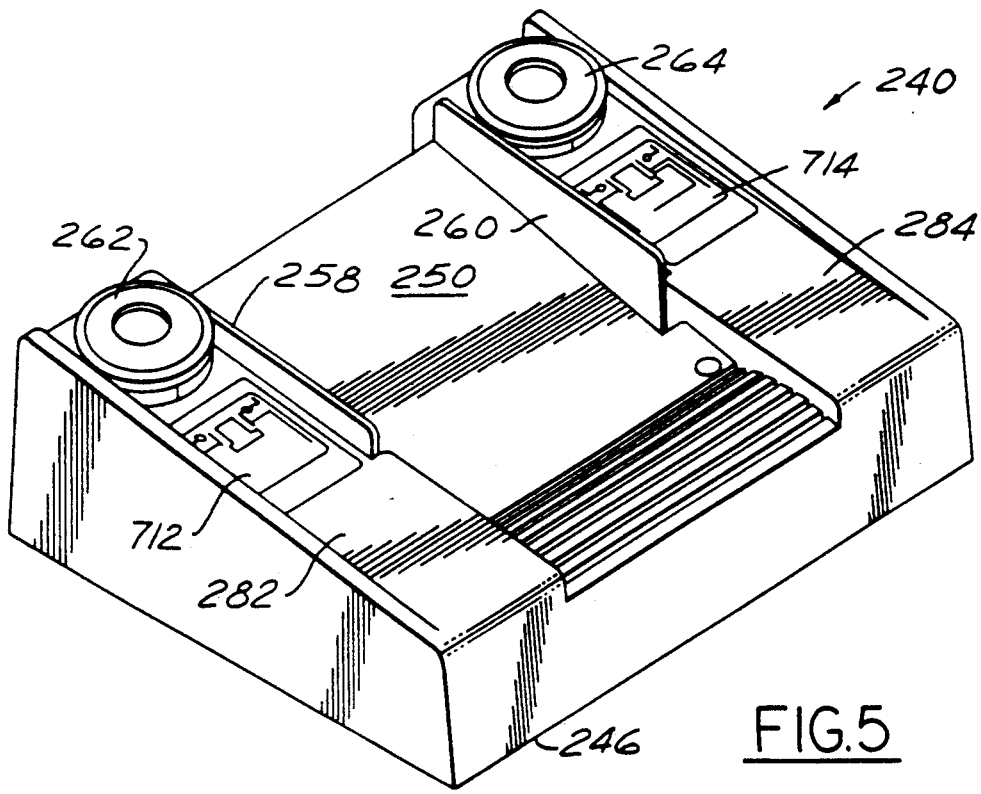
FIG.5
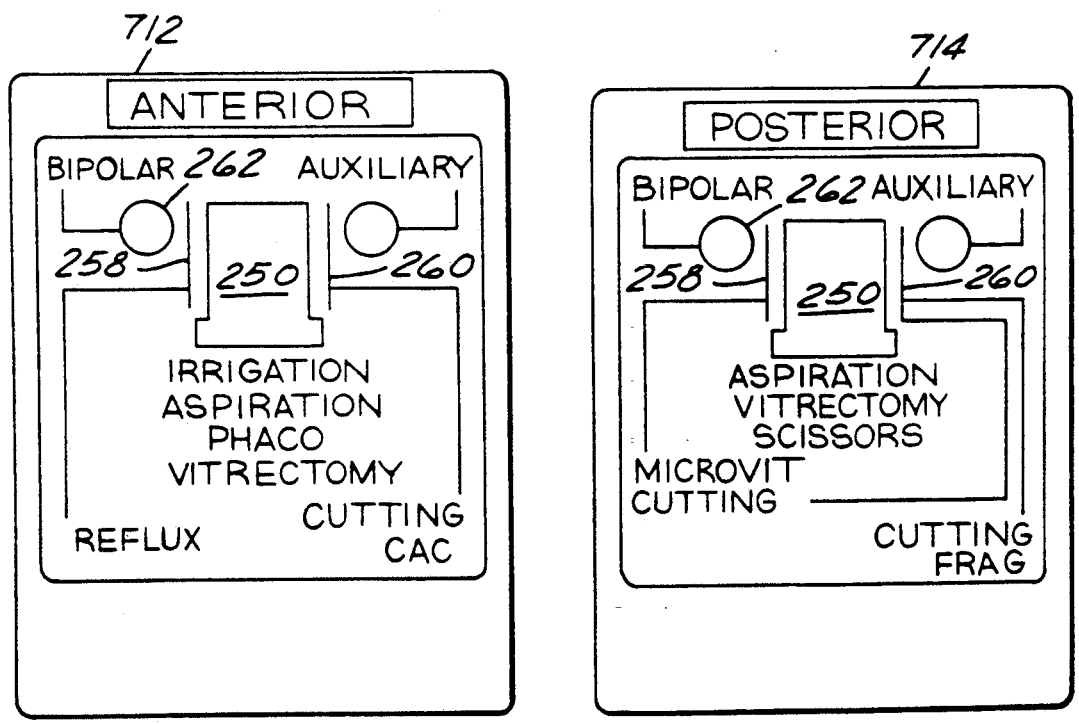
FIG.6
FIG.7

FOOTSWITCH ASSEMBLY WITH ELECTRICALLY ENGAGED DETENTS

CROSS-REFERENCE TO RELATED APPLICATIONS

The present invention is related to the subject matter of the following commonly assigned co-pending applications:

U.S. patent application Ser. No. 07/251,531, filed Sept. 30, 1988 in the name of Kevin L. Klug and entitled "Phacoemulsification Probe"; and U.S. patent application Ser. No. 07/267,713 filed Nov. 4, 1988, which is a continuation of U.S. patent application Ser. No. 06/928,170 filed Nov. 6, 1986 and entitled "Control System For Ophthalmic Surgical Instruments."

The present invention is also related to the subject matter of the following commonly assigned applications being filed concurrently on even date herewith:

U.S. patent application Ser. No. 428,232, filed Oct. 27, 1989, entitled "Control System For Ophthalmic Surgical Instruments";

U.S. patent application Ser. No. 427,614, filed Oct. 27, 1989, entitled "Remote Control Console For Surgical Control System";

U.S. patent application Ser. No. 428,125, filed Oct. 27, 1989, entitled "Vitrectomy Probe";

U.S. patent application Ser. No. 428,216, filed Oct. 27, 1989, entitled "Modular Cabinet For Surgical Control System"; and U.S. patent application Ser. No. 428,166, filed Oct. 27, 1989, entitled "Motorized IV Pole Assembly."

The disclosures of each and every one of the above-referenced applications is hereby incorporated herein by reference.

FIELD OF THE INVENTION

The present invention relates generally to microsurgical and ophthalmic systems, and more particularly to a footpedal assembly for use with a control system for operating microsurgical instruments.

DESCRIPTION OF RELATED ART

Ophthalmic microsurgical systems typically provide one or more pneumatically operated (fluid pressure operated) surgical instruments connected to a control console. The control console provides the fluid pressure signals for operating the instruments and usually includes several different types of human actuatable controllers for controlling the fluid pressure signals supplied to the surgical instruments. Usually included is a footpedal assembly which the surgeon can use to control a surgical instrument.

Conventional footpedal assemblies use a variety of pneumatic and electrical actuators to control microsurgical instruments. In pneumatic footpedal assemblies, pneumatic fluid enters the footpedal assembly through an inlet port which is connected to a pneumatic supply. The amount of pneumatic fluid leaving the footpedal assembly is proportional to the amount of depression on the footpedal of the assembly. The larger the depression on the footpedal, the greater the amount of pneumatic fluid which is delivered to the control console from the footpedal assembly. Footpedal assemblies which employ electrical actuators use a potentiometer which is attached to the pedal. As the pedal is pivoted by the operator, the resistance of the potentiometer changes. This change in resistance is used by the control console to generate a signal for adjusting the microsurgical instruments.

While conventional footpedal assemblies have helped to make microsurgery and ophthalmic surgery possible, these assemblies are not without drawbacks. Such footpedal assemblies often become inoperable when they were exposed to saline, which is used in ophthalmic microsurgical procedures, and therefore were often unreliable. In addition, because such footpedal assemblies provided an analog input to the control console, the footpedal assemblies were not generally capable of providing a high resolution positional signal that would otherwise be possible with a digitally encoded signal. Thus, footpedal assemblies utilizing digitally encoded signals, offer a number of advantages.

However, even digitally encoded footpedal assemblies are limited in their usefulness if they only operate in a single mode throughout the range of footpedal travel. Thus, it would be desirable to have a footpedal assembly in which the surgical system is operated in multiple modes throughout the range of travel of the footpedal. One problem with such a system would be to inform the operator of which mode the footpedal was in. One approach to this problem is through the use of detents.

Use of detents in footpedal assemblies is known in the surgical arts, for example, in ophthalmology. In one prior art footpedal, an electrically actuated solenoid clapper is used to produce a mechanical clicking sound by extending a solenoid armature outwardly and back. This results in a noticeable click sound which is heard by the surgeon operating the foot switch. However, this extraneous noise can prove objectionable to some surgeons. This detent arrangement also provides some tactile feedback to the surgeon, especially for those surgeons who prefer to operate the pedal without shoes for increased sensitivity to pedal movement. However, even though the clicking of the solenoid may be felt, as well as heard, this only lasts momentarily so that the surgeon may forget which range of pedal motion he is in. Thus, it would be desirable to have a tactile feedback system in a footpedal assembly which would enable the surgeon to tell by feel which operating range of the pedal he was in.

Accordingly, it is an object of the present invention to provide a foot switch assembly which provides a different tactile feedback in each of the different ranges that the footpedal operates in. It is a further object of the present invention to provide a footswitch in which such tactile feedback is continuous as opposed to momentary.

Some modes of operation of surgical instruments require detents, since multiple modes are desired throughout the range of footpedal motion. On the other hand, other modes of operation may require only a single mode throughout footpedal travel. For example, one surgical function which is performed without the use of detents is linear aspiration. This is most commonly employed in surgical procedures using a vitrectomy, such as the guillotine cutter type probe available from Storz and sold as the MICROVIT vitrectomy probe. In one mode of operation, the cut rate of the guillotine cutter, within the probe, is set to a constant value, such as 200 cpm, and the footpedal is used to adjust the vacuum level used to suck material to be cut, such as bloody vitreous, from the eye. In this mode of operation, no detents are used, but instead the suction level is varied linearly, with pedal position.

One example of multimode functions requiring detents is phacoemulsification, where at least three distinct functions are required. These are: irrigation., aspiration., and phacoemulsification. Thus, with detents, a single footpedal may be used to control these three functions. Thus, it would be desirable to have a footswitch assembly which is reconfigurable for single mode operation, without detents, and for multiple mode operation, with detents.

Accordingly, it is an additional object of the present invention to provide a footswitch assembly which can be adopted for single mode as well as multiple mode (detent) operation.

SUMMARY OF THE INVENTION

In light of the foregoing desires and objects, there is provided in accordance with the present invention, a footswitch apparatus for remotely controlling an instrument, including a base, a footpedal movably mounted to the base and a means for limiting the range of motion of the footpedal within upward and downward limits. Also, a first and second resilient means are provided for resisting the movement of the footpedal in one direction, and for returning the footpedal to one of the limits in the other direction. The first resilient means will provide a first resistent force in a first range of movement of the footpedal, the second resilient means will provide a second resistent force in a second range of movement. In addition, a means responsive to the movement of the footpedal is provided for altering the operation of the instrument when the footpedal travels from one of the ranges to the other.

In addition, the footswitch apparatus may be provided with a means for selectively decoupling the second resilient means so that only the first resistent force is provided throughout the range of motion. In this way, the operator of the instrument is given continuous tactile feedback as to which zone of travel the footpedal is in. These and other aspects, objects, features and advantages of the present invention will be better understood by considering the detailed description below and the appended claims in conjunction with the drawings.

BRIEF DESCRIPTION OF THE DRAWINGS

The drawings form an integral part of the description of the preferred embodiments and are to be read in conjunction therewith. Like reference numerals designate the same or similar components or features in the various FIGURES, where:

FIG 2 is a front view of the FIG. 1 control console showing the layout of the CRT visual display, control buttons or keys, surgical instrument connection ports and the like;

FIG. 5 is a perspective view of the footswitch assembly in accordance with the present invention;

FIG. 6 is a view of the functionality legend for anterior surgical procedures located on the left side of footswitch assembly shown in FIG. 5;

FIG. 7 is a view of the functionality legend of the functions of the footswitch system for posterior surgical procedures located on the right side of the footswitch assembly shown in FIG. 5;

DETAILED DESCRIPTION OF THE PREFERRED EMBODIMENT

I. General

A. Front of Control Console (FIG. 1A)

1. Display & Keys Of Primary Panel

Figure 1A:
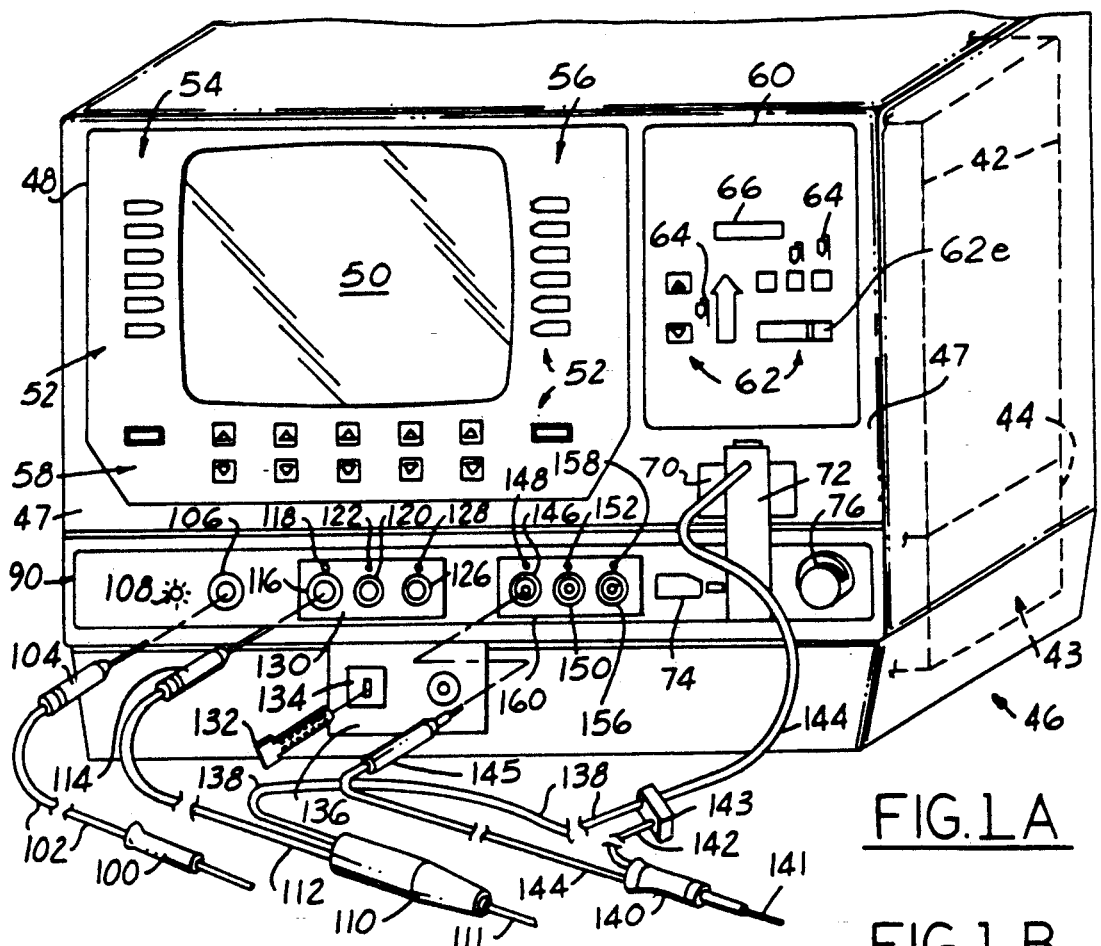
FIGS. 1A and 1B are front and back perspective views of an ophthalmic microsurgical control console which utilizes the pneumatic control system of the present invention.
Figure 1B:
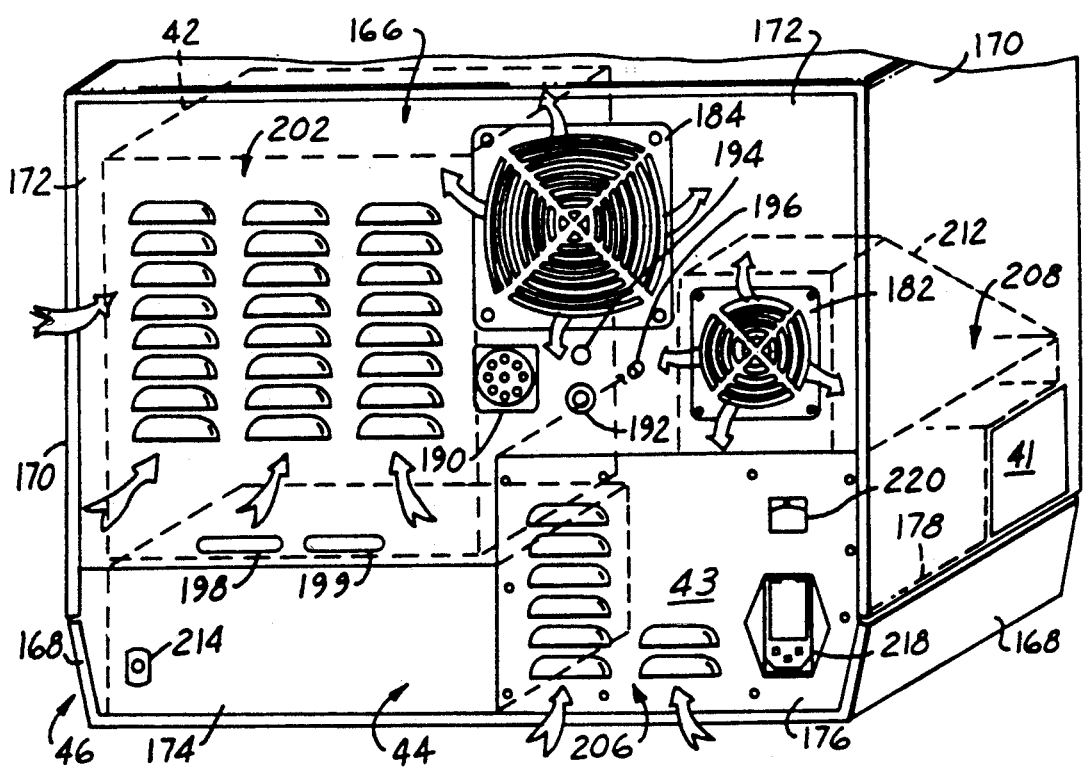
Figure 2:
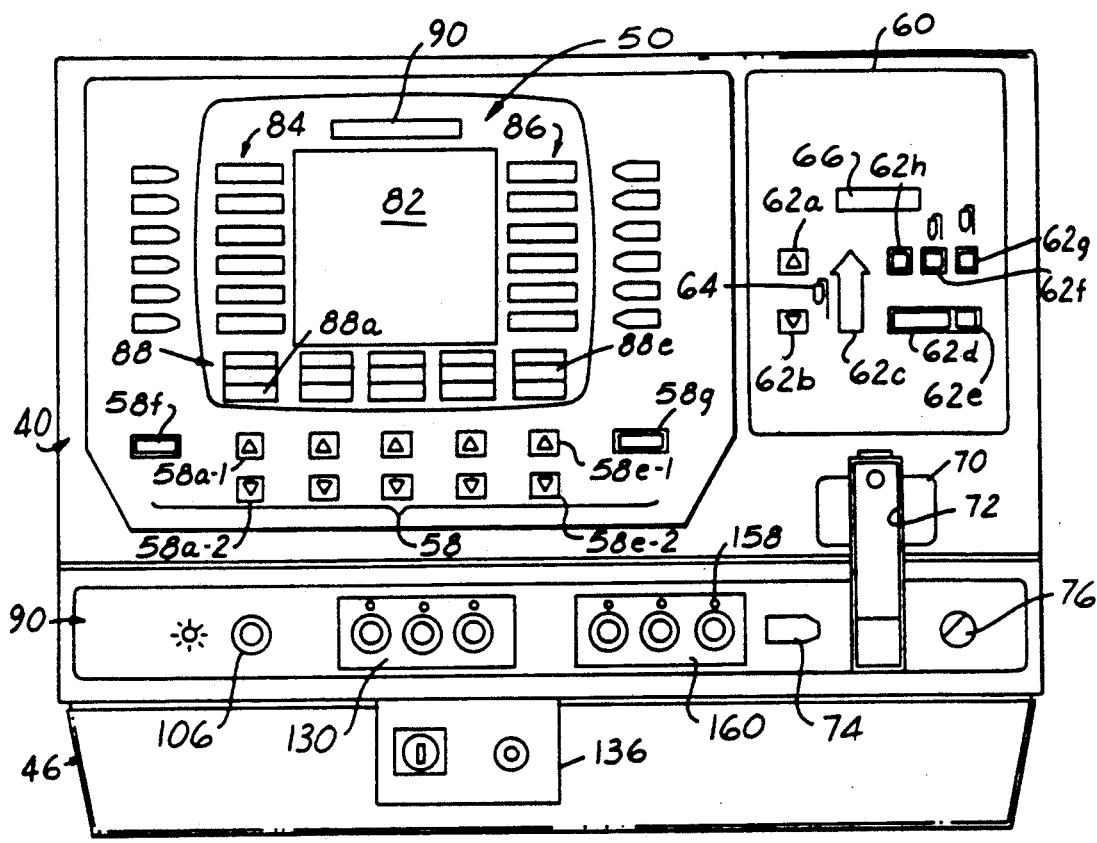

FIGS. 1A, 1B and 2 show a microsurgical control system 40 provided with an illumination lamp drawer 41, an electronic control system housed in part in a nine-board electronic card rack 42, and a pneumatic control system 43 housed primarily in a pneumatic drawer module 44, and other modules which will be described later. The control system 40 includes a system console 46 which has an upwardly and slightly inwardly-sloping front surface 47 with a primary front panel 48. On the front panel 48 is an electronic display screen 50, a plurality of pushbuttons or touch sensitive pads 52 organized in two groups 54 and 56 along the left and right sides of the display screen 50, and a third group 58 along the bottom of the display screen 50. Additionally, there is a secondary front panel 60 located to the right of front panel 48 which has additional pushbuttons or pads 62, indicator lights 64 and information readout 66. The console 46 also includes a slot 70 for a conventional Storz aspirant collection cassette 72, a cassette eject button 74 and an irrigation pinch valve assembly 76.

The electronic display screen 50 is controlled by a microcomputer within the console 46 to provide several different menus or messages which instruct the operator as to the function of the pushbuttons 52 through 62. The operation of the display screen 50 in combination with the buttons 52-62 may be best understood by looking at the enlarged view in FIG. 2. The display screen 50 is shown there as being conceptually divided into central display screen region 82, left-side display region 84, right-side display region 86, bottom display region 88 and a top display region 90. The side regions 84 and 86 each consist of six horizontal fields stacked one above the other and positioned to correspond to the locations of buttons in button groups 54 and 56. By virtue of the adjacent location of the top button of button group 54 and the top field of region 84, for example, a message in the upper left-hand corner of the screen 50, i.e., in this top field, is readily understood by the operator as referring to the upper leftmost button. The other buttons and fields are similarly paired. This arrangement allows the indicated function of each of the buttons 54 or 56 to be readily changed by simply just changing the legend displayed in its adjacent field. In a similar manner, each pair of buttons, such as buttons 58a-1 and 58a-2, is associated with one of the three-part fields of bottom region 88, such as region 88a. In general, the upper row of buttons, i.e., buttons 58a-1 through 58e-1 are used to increment a setting or parameter displayed in the corresponding region 88a-88e of screen 50 directly above, while the buttons in the lower row, i.e., buttons 58a-2 through 58e-2, are used to decrement such displayed settings or parameters. The use of an electronic display screen also permits the legends for buttons 52, 54 and 56 to be labeled in virtually any language. Button 58f is used to bring up an information screen on display 50 to assist the operator, such as by further explaining functions associated with choices on the display menu. Button 58g is used to return to an earlier menu screen in a chain of related menus or other screens.

2. Surgical Instrument Connector Panel

The microsurgical control system 40 is capable of operating a number of different microsurgical instruments. To provide for this functionality, there is a row of different types of connector receptacles on surgical instrument connector panel 90 which permits various instruments to be plugged in or otherwise controlled by the control system 40 as may be seen in FIGS. 1A and 2, indicator lights are provided adjacent to or above each of the connector receptacles for indicating when the connector is activated or functional.

a. Illumination Instrument

FIG. 1A shows a fiber-optic illumination instrument 100 coupled to console 46 via fiber-optic cable 102 which extends out of male illumination connector plug 104 designed for insertion into illumination connector receptacle 106. Indicator lamp 108 is illuminated whenever the fiber optic illumination (FOL) lamp inside console 46 is lit.

b. Electrically Powered Instruments

Phaco fragmentation handpiece 110 is a conventional piezoelectric device for disintegrating hard objects such as intraocular cataractous material utilizing ultrasonic ("US") energy transmitted to its needle III. Electrical power pulsating at US frequency is provided to handpiece 110 via power cable 112 attached to phaco connector plug 114, which is designed to be inserted into phaco female connector 116. Light 118 indicates when US frequency electrical power is being delivered to 116.

Female connector 120 is designed to receive a male connector plug (now shown) for powering a conventional bipolar coagulator handpiece. Indicator light 122 indicates when this connector 120 is operational. Female connector 126 is used for receiving a male connector plug (not shown) of a conventional CAC handpiece. (GAC stands for "controlled anterior capsulotomy.") Indicator 128 illuminates when the CAC function is activated. Thus it will be seen that the three connectors 116, 120 and 126 grouped together on rectangular plate 130 all relate to electrically powered surgical functions.

c. Fluid-Powered Instruments

Certain microsurgical instruments are actuated or controlled by fluid pressure (either positive pressure or negative pressure, or both). The phaco fragmentation instrument 110, for example, utilizes aspiration through hollow flexible plastic tubing 138 to remove disintegrated materials, which are collected along with aspirant in the cassette 72.

Vitrectomy probe 140 includes a hollow needle 141 having an inner tube which reciprocates to cut intraocular material sucked in a small hole near the tip of the needle. The inner tube (not shown) reciprocates on account of pulsating air pneumatic drive signal delivered to a spring-returned piston (not shown) to which the inner tube is connected. The suction part of this instrument is also coupled to the collection container 72 by tubing 142. (Bracket 143 is intended to indicate that either tube 142 or tube 138 may be connected to the remaining portion of tube 144 which leads to the collection cassette 72.) Tubing 144 extending from the probe 140 leads to male connector plug 145 which is inserted into vitrectomy connector receptacle 146. Light 148 indicates when the connector is activated. Connector 146 supplies the pulsating air drive signal to the vitrectomy probe from a pneumatic circuit which will later be described. A conventional vitrectomy probe in the form of a guillotine cutter such as the Storz MICROVIT® probe may be used. Alternatively, the improved probe described in aforementioned U.S. patent application Ser. No. 428,125, filed Oct. 27, 1989 entitled "Vitrectomy Probe" may be used as probe 140.

Connector receptacle 150 provides access to an intraocular pressure (IOP) system (not shown), and indicator light 152 indicates when connector 150 is actuated. Connector 156 is used to deliver a pneumatic drive signal to conventional pneumatically operated microscissors (not shown), which can be operated in any one of three modes as will be further explained. Indicator light 158 is illuminated when any one of the three scissors modes is enabled. In light of the foregoing description, it will be appreciated that the three connectors 146, 150 and 156 located on rectangular plate 160 all relate to surgical functions implemented via the pneumatic system of console 46.

While certain microsurgical instruments have been illustrated or described in connection with FIG. 1A, it should be understood that the microsurgical control system 40 can be used with other instruments of a similar type. In general, any microsurgical instrument that is actuated or controlled by fluid pressure (whether positive or negative), can be made to operate with the pneumatic control system of the present invention.

d. Irrigation Pinch Valve

The irrigation pinch valve assembly 76 is utilized to provide on/off control for the gravity-infused salt solution held in the IV bottle. The pinch valve is operated by an on/off solenoid of the pneumatic system as will be further explained. Display 66, which may be an LED display or the like, indicates the height of the IV pole above the minimum reference height established via the zero switch 62e.

3. Off-line Memory Storage of User Data

On occasion, it is desirable to store selected operating values or set-up parameters for a particular surgeon or microsurgical operation in off-line memory. A removable memory key 132 is provided for this purpose. The key 132 includes an integrated memory circuit which stores such operating values or set-up parameters. Console 46 receives the key 132 through a key receptacle interface 134 mounted in plate 136. Suitable types of memory keys and receptacle interfaces are commercially manufactured by Datakey, Inc. of Burnsville, Minn. However, it should be appreciated that other suitable means for storing particular user data may be employed with the console 46 as well, such as electronic cards with memory, magnetic disk media, or the like.

4. Display & Keys Of Secondary Panel

(FIG. 2)

The functions associated with the secondary panel 60 will now be described. As best seen in FIG. 2, panel 60 is used to control a motorized IV pole (not shown) that supports one or more bottles or pouches of balanced salt solution used to provide irrigation during ophthalmic surgical procedures. The motorized IV pole includes a reversible electric motor/gear reducer combination which adjusts the height of the IV pole up or down as desired. The particular height may be selected via the buttons on control panel 60. Buttons 62a and 62b are used to lower and raise the pole incrementally, as long as the button is held. Button 62c is used, under emergency conditions, to send the pole upward rapidly to its maximum height, and indicator emblem 64 is illuminated when this function is activated. Button 62d, when depressed, automatically lowers the IV pole to a convenient height to facilitate changing of the IV bottle. Button 62e is called the "zero switch" because when pressed it establishes the zero reference, i.e., the minimum height for the IV pole. Button 62f and 62g are used respectively to change the height for the IV pole to either a first or second preset level. Button 62h is used during set-up to specify the first and second preset heights of the IV pole. The operation of these functions and the construction of the "Motorized IV Pole Assembly" is described in aforementioned U.S. patent application Ser. No. 428,166, filed Oct. 27, 1989 of the same title.

B. Rear of Control Console

(FIG. 1B)

FIG. 1B shows the rear of the system console 46, including the rear surface 166. The console 46 includes a base frame or chassis 168, a sheet metal cover 170 having three sides forming an inverted U-shape, and back cover plate 172 occupying roughly the top two-thirds of the surface 166. The bottom one-third of the rear surface 166 is occupied by the rear wall 174 of pneumatic drawer module 44 shown in phantom, and the rear wall 176 of electrical power drawer 178 which is also partially shown in phantom and will be later described. Mounted on the upper rear cover plate 172 are the following devices: small ventilation fan 182, a large ventilation fan 184, an electrical connector receptacle 190 for a footpedal controller, an IV pole connector receptacle 192, an accessory connector receptacle 194 and a CRT screen brightness control knob 196. Cover slots 198 and 199 are also provided for future expansion to allow addition of RS232 communication ports. Rear cover plate 172 includes a set 202 of 24 ventilation louvers arranged in three columns. Rear wall 176 of power electrical drawer 178 includes a set 206 of eight ventilation louvers arranged as shown. Both sets 202 and 206 of louvers allow air to be drawn inside of the console 46. Air drawn in through louvers 202 circulates internally and eventually exits at exhaust fan 184, while air drawn in through louvers 206 is substantially confined to circulate within the electrical drawer 208 and past the lamp drawer 41 since it is confined by shelf/cover 208 and plenum 212 to be exhausted by ventilation fan 182.

The main pneumatics supply connection to pneumatics drawer 44 is made through a male Schrader quick-disconnect fitting 214 in the lower left rear corner of rear wall 174. Electrical power is provided to the electrical drawer module 178 via electrical receptacle and fuse holder assembly 218. A main on/off electrical power switch 220 for turning the console 46 on or off, is located above receptacle 218. The various hardware assemblies and drawers of console 46 are constructed in a highly modular, easy-to-assemble and easy-to-service manner described in detail in aforementioned U.S. patent application Ser. No. 428,216, filed Oct. 27, 1989, entitled "Modular Cabinet For Surgical Control System."

II. Surgical Modes & User Interface In General

A. Switch-Selectable Surgical Modes & Features

The control console 46 is the heart and brain of the multi-function microsurgical system 40. The system 40 supports up to nine switch-selectable modes which are used in either or both anterior segment and posterior segment ophthalmic surgery. These modes are: (1) irrigation only, (2) irrigation/aspiration, (3) phaco (either emulsification or fragmentation), (4) vitrectomy, (5) controlled anterior capsulotomy (CAC), (6) bipolar, (7) scissors, (8) illumination, and (9) intraocular pressure (IOP) control. Each mode is automatically integrated into the system 40 in a manner appropriate to the type of operation selected by the operator via keys 52–58. 1. Irrigation mode employs a footpedal on/off control of irrigation. This operating mode is intended for use during an anterior capsulotomy and other anterior segment procedures in which irrigation without aspiration is desired. 2. Irrigation/aspiration mode provides footpedal on/off control over irrigation and linear footpedal control over aspiration. This mode is intended for use in the engagement, stripping and removing of residual lens cortical material in extracapsular cataract extraction and phacoemulsification procedures. 3. Phaco mode implements the phacoemulsification and phacofragmentation functions, which are available for both anterior and posterior segment procedures. Under phacoemulsification procedures, a "fixed phaco" mode is available in which the phaco power and aspiration levels are set via the console controls, and "linear phaco" mode is available in which phaco power is footpedal controlled and aspiration level is determined by the console controls. For phaco fragmentation procedures, a fixed phaco mode controls aspiration via the footpedal. 4. Vitrectomy mode makes the vitrectomy function is available for both anterior and posterior segment procedures. For anterior vitrectomy, footpedal on/off control is provided for vitreous cutting and irrigation, while linear footpedal control is provided for aspiration. For posterior vitrectomy, this mode provides footpedal/on-off control over vitreous cutting and linear footpedal control over aspiration. 5. CAC mode provides footswitch on/off control of a CAC probe, and is explained further in connection with the discussion FIG. 4D below. 6. Bipolar mode provides on/off control of bipolar power via the footpedal assembly, and is described further in the discussion of FIG. 4D below. 7. Scissors mode enables the posterior surgeon to employ a pneumatically driven intraocular scissors in any one of three foot-pedal controlled cutting operations: single cut, variable rate or proportional, which will be explained in more detail later. 8. Illumination mode provides fiber-optic illumination to facilitate viewing the posterior segment during posterior procedures. The light source thereof is adjustable from approximately five-percent illumination to full brilliance. Automatic lamp switching provides back-up illumination if the primary lamp should fail. 9. IOP mode provides precision regulated console-adjusted delivery of filtered air to the eye during posterior ocular pressure procedures. Alternatively this mode can be used to pressurize an irrigation supply to the eye for anterior procedures.

Many of the foregoing modes and features are also found in the DAISY opthalmic system marketed by Storz Instrument Company, St. Louis, Mo. For example, like DAISY console, console 46 uses a disposable transparent cassette to collect aspirant during surgery. When the cassette is fully inserted into the cutout slot 70 in the console 46, the system 40 will automatically secure the cassette via a solenoid-actuated valve, and a vacuum connection will be established at that time. 10. Additional Surgical Features. The system 40 also includes additional features, namely, aspiration prime and irrigation prime in the same manner implemented in the DAISY ophthalmic system. Further, the special repeat reflux procedure is supported by the control console 46 in order to allow a handpiece to be cleared with pneumatic pressure if it becomes clogged with tissue. This reflux feature is available in all anterior modes, and consists of repeated reflux action.

B. User Interface Strategy

The integration of all of the aforementioned functions into a single console 46 represents a formidable organizational challenge since the system 40 must provide the operator(s) with a straight forward means of invoking all of the different modes, the functions under each mode, and a way to adjust the various set-up and operating parameters associated with various electronic control circuits and pneumatic control systems. The CRT display and pushbutton arrangement assists system flexibility greatly in this regard since it is possible to reprogram the functions of the switches 52 in accordance with the selected anterior segment or posterior segment procedure or with the selected utility functions, such as establishing set-up values or configuring the system for a particular surgeon's use.

Similarly, the use of a microprocessor-based control system, described in FIG. 4, enables the various strategies for the control functions to be stored in memory and called upon as required. To reduce cost of construction and assembly time, and to increase reliability and serviceability, the various components of the surgical system have been constructed as separate modules or subassemblies where possible. This approach is evident in the electronics portion and pneumatics portion of the control system 40. Where practical, distinct electrical functions have been placed on their own printed circuit board which is separately addressed by the microprocessor. Similarly, the pneumatics functions have been collected and placed in one drawer module to allow easy installation and replacement.

III. Footswitch Assembly

(FIG. 3)

Figure 3:
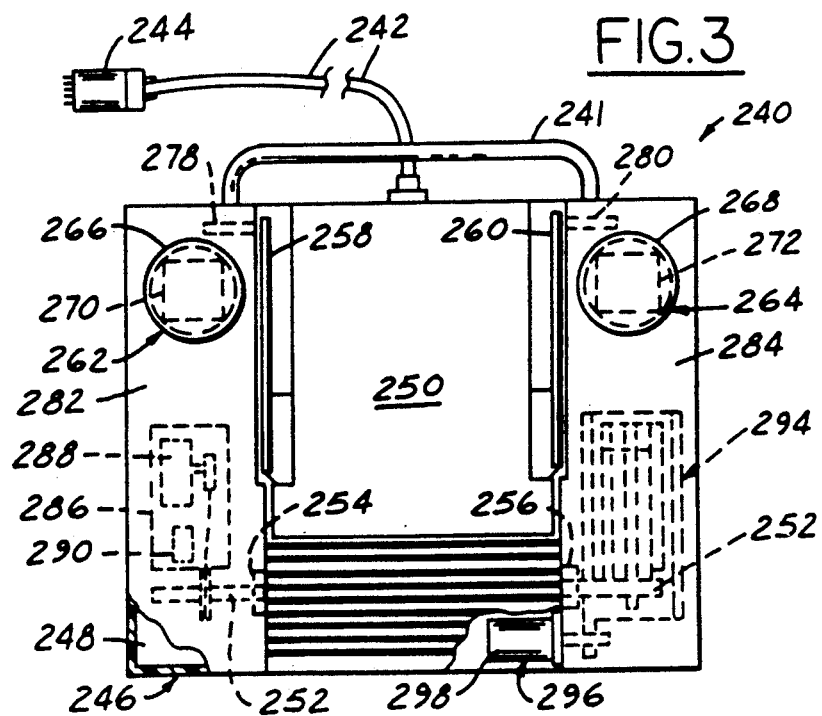
FIG. 3 is a plan view of the footswitch assembly usable with the present invention.

FIG. 3 shows a plan view of foot controller 240 (also called a footswitch assembly) utilized by the system 40 which has a metal carrying handle 241 and is linked directly to the console 46 with a suitable length of multi-conductor electrical cable 242 which has suitable multi-pin connector 244 at the end thereof that plugs into connector receptacle 190 on the back of the console 46. The footswitch assembly 240 includes: a large plastic molded housing 246 enclosed with a large rectangular bottom plate 248; having a footpedal 250 which pivots about a horizontal footpedal shaft 252 supported by sintered bronze flange bushing assemblies 254 and 256; left and right vertically arranged side pedals 258 and 260; and left and right top footswitch assemblies 262 and 264 having mushroom heads 266 and 268 and electrical contact blocks 270 and 272, shown in phantom, to signal when the respective top buttons have been pushed. Side switches 278 and 280, which may be microswitches or magnetic proximity switches, shown in phantom, are actuated and provide electrical signals indicating when their respective side pedals 258 or 260 have been pressed. The housing 246 includes left and right bunker structures 282 and 284 which rise above footpedal 250 upon which top footswitches 262 and 264 are mounted. Underneath left bunker 282 is located a footpedal position encoder assembly 286 shown schematically in phantom. Assembly 286 includes an optical position encoder 288 which produces two digital signals in a quadrature relationship as the shaft 252 rotates, and a zero reset switch 290. Under bunker 284 is located a detent assembly 294 which may be electrically engaged as desired via detent control solenoid assembly 296 including an electrical solenoid coil 298. The side switches 278 and 280 and top footswitches 266 and 268 provide on-off control of certain features during selected ophthalmic procedures. For example, the left top footswitch 266 provides on/off control of bipolar coagulation. The right top footswitch 268, via display 50 and buttons 52, may be configured to control the emergency rapid-up feature of the motorized IV pole option or to control some other operating room device via the accessory receptacle 194 on the back cover 166 of console 46. In anterior segment procedures, the footpedal is used to control irrigation, aspiration, phaco and vitrectomy modes in a manner like that used for the Storz DAISY console. However, the footpedal detents are new and are provided in the manner described below to provide the surgeon with tactile feedback regarding the footpedal position.

IV. Electronic Control System

(FIG. 4)

A. General Overview of Electronics Hardware

(FIG. 4A)

Figure 4A:
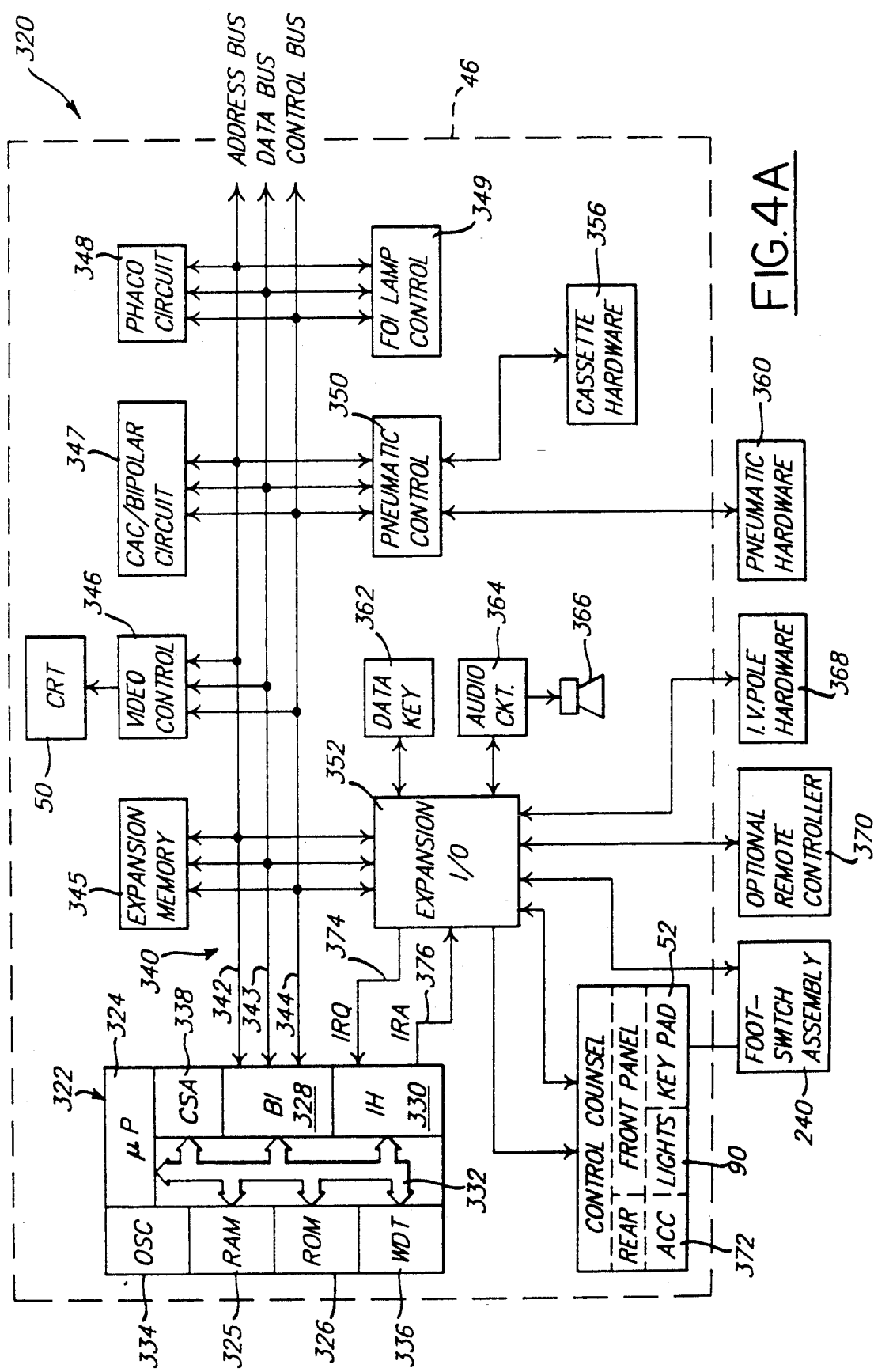
FIG. 4A is a simplified block diagram of the microprocessor-based electronic control system of the FIG. 1 control console showing how information is passed electronically between the microprocessor and the various boards and devices within the over-all surgical system.

FIG. 4A shows a simplified block diagram of a microprocessor-based electronic control system 320 found in the control console 46 shown in FIG. 1. Control system 320 includes a microcomputer 322 having a microprocessor 24, volatile (RAM) memory 325, nonvolatile (ROM) memory 326, a VME bus interface circuit or port 328, an interrupt handling circuit or port 330, and an internal control/address/data bus 332 which allows internal communications in conventional fashion between all portions of microcomputer 322. A preferred microprocessor 324 is a 68000 Series Motorola microprocessor with a clock speed of 12.5 Megahertz and one wait state for handling interrupts, although any other suitable microprocessor could be used. Computer 322 also includes a 25 Megahertz crystal oscillator 334, a watchdog timer circuit 336, and a chip select and addressing (CSA) section 338. The microcomputer 322 is located on a single board, called the processor board.

The microcomputer 322 which is located on its own printed circuit (PC) board, communicates with the remainder of the electronic control system 320 via a VME bus 340 consisting of address, data and control lines 342, 343 and 344. The VME bus 340 is used to communicate with seven other boards within the system 320, namely: the expansion memory PC board 345, the video control PC board 346 which drives the visual display 50, the CAC/bipolar circuit PC board 347, the phaco circuit PC board 348, the lamp control PC board 349, the pneumatic control PC board 350, and the expansion I/O PC board 352.

The groupings of various functions on distinct PC boards was done in order to make maintenance simpler. By clustering similar or related functions together on one board, it is possible to reduce diagnostic time and service costs since individual functions not performing correctly may be isolated on a board-by-board basis, and suspect boards may be replaced as needed. The processor board 322, the expansion memory board 345 and the video board 346 are all conventional purchased items from PEP Modular Computers GmbH of Kaufbeuren, West Germany. The manner in which all of these boards are designed and work from a hardware and operating system perspective is conventional. The manner in which the video board 346 drives the CRT 50 is conventional too. The CRT 50 used with the control console 46 is preferably a 9-inch diagonal monochrome monitor with standard resolution, although any other suitable two-dimensional display may be utilized such as liquid crystal display or electro luminescent display.

The lamp control board 349 is used to control the components in the lamp drawer 41 which is the source of light for fiber optic light pipe 100 shown in FIG. 1A. Pneumatic control board 350 is used to control the cassette hardware 356 and the pneumatic drawer hardware 360. The cassette hardware 356 refers to those input devices such as switches and output devices such as solenoids associated with the aspirant collection cassette 72 shown in FIG. 1A. The pneumatic hardware includes pressure transducer, a torque motor servovalve and solenoids.

Expansion I/O board 352 is used to communicate or control the memory key circuit 362, the audio generator circuit 364, which drives speaker 366, the IV pole hardware 368, an optional remote controller 370, and the footpedal assembly 240 of FIG. 3. The expansion I/O board 352 also is used to interrogate or operate various other input and output devices associated with the control console 46, such as the keypads 52, the indicator lights on secondary panel 60 and connector panel 90 and the accessory relay 372 associated with accessory receptacle 194 shown in FIG. 1A. All user-generated input commands are handled through I/O board 352. To ensure such commands are promptly communicated to the processor 324, board 352 generates an interrupt request (IRQ) signal on line 374 to inform the processor 324 that the I/O board needs to be serviced. The processor also generates an interrupt acknowledge (IRA) signal on line 376. In this manner, user input commands take precedence over lower priority I/O tasks also being handled via VME bus 340.

B. Expansion I/O Board Circuit (FIG. 4B)

1. Introduction

Figure 4B:
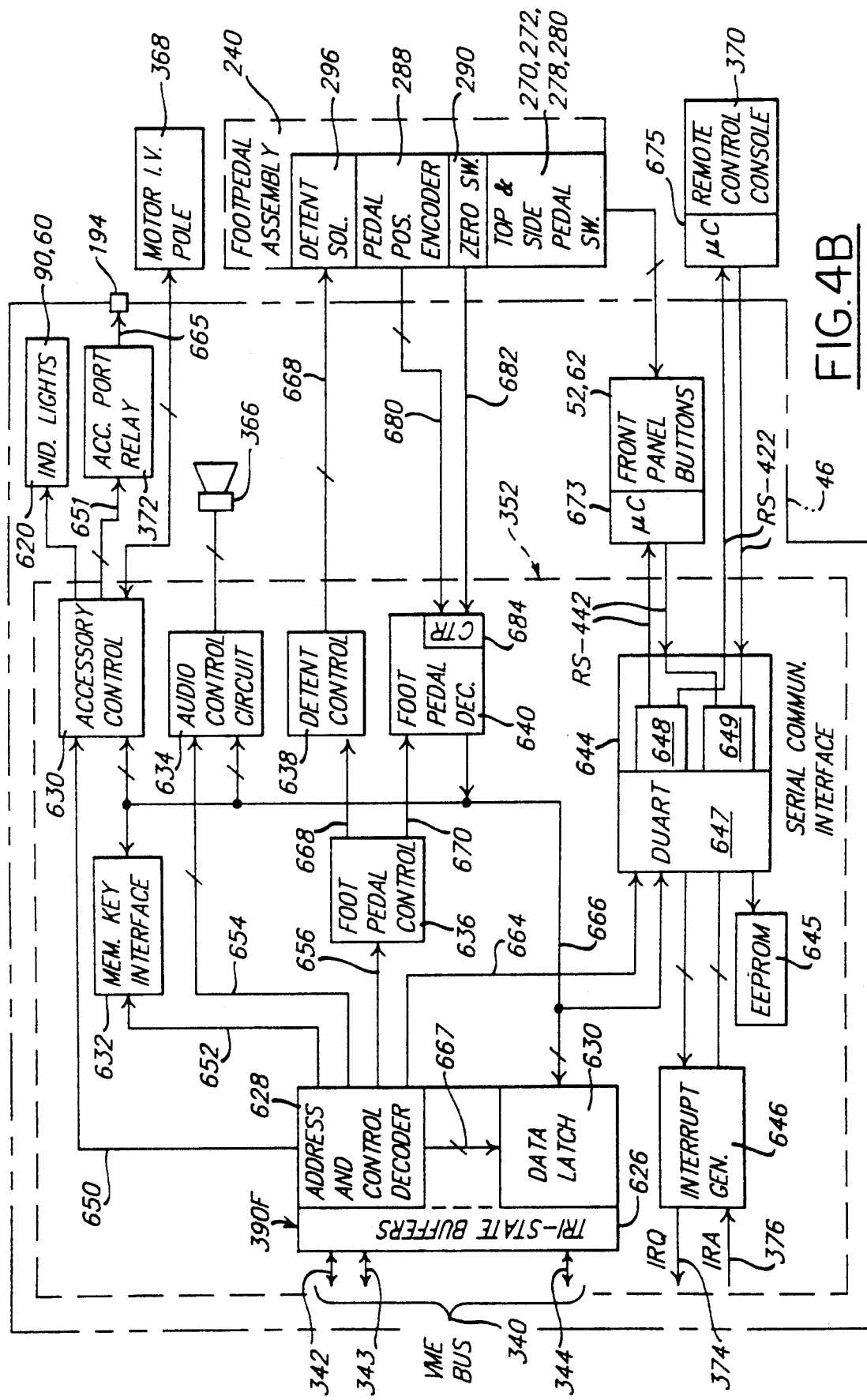
FIG. 4B is a detailed block diagram of the I/O expansion board shown in FIG. 4A and the electrical equipment interfaced therewith.

FIG. 4B shows a detailed block diagram of the I/O expansion board 352 and the devices which it drives or reads, namely: the indicator lights on secondary front panel 60 and on connector panel 90 (represented by block 620) and relay 372 for accessory connector 194, the speaker 366, and the primary and secondary front panel buttons 52 and 62, all of which are located in or on the control console 46 (indicated by these devices being to the left of the dashed line 46, which represents the perimeter of control console 46). The board 352 also drives and/or reads devices in the motorized IV pole assembly 368, the footpedal assembly 240, and the optional remote control console 370, which are all outside of the control enclosure 46.

The I/O board 352 communicates with the VME bus 340 through a VME interface 390f which includes tri-state buffer circuits 626, address and control decoder circuit 628 and 16-bit data latch or register 630. The I/O circuitry on board 352 also includes four primary control interface circuits, namely accessory control 630, memory key control 632 for memory key 132, audio control 634 for speaker 366, and footpedal control 636. Control circuit 636 in turn directs the operation of two slave circuits, namely detent control 638 and footpedal decoder 640 which actually communicate with devices in footpedal assembly 240. Board 352 also includes a conventional serial communications interface circuit 644 which drives and reads in conventional fashion an interrupt generator circuit 645 and a non-volatile memory 646, which preferably is an electrically erasable programmable read only memory (EEPROM). Circuit 644 includes three conventional integrated circuit (IC) chips, namely a dual universal asynchronous receiver/transmitter (DUART) 647, a dual-channel RS-422 transmitter chip 648, and a dual-channel RS-422 receiver chip 649, all functionally connected as shown in FIG. 4F.

The primary interface circuits 630.638 and the serial communications interface 644 communicate with VME bus interface 390f via control signals passed along dedicated control lines 650–656 and 664. Data to be sent to and/or received from circuits 630–638 or communications interface 644 is passed along an internal 16-line data bus 666 connected to data latch 630. Footpedal control 636 communicates with slave circuits 638 and 640 via lines 668 and 670. Each of the primary control circuits and the communications interface 644 contains a data latch circuit for receiving, holding and/or transmitting data to internal data bus 666.

Address and control decoder 628, upon receipt of commands from processor 324 via VME bus 340, decodes the command and address signals on lines 342 and 343, and in accordance with the decoded instructions distributes the desired control signals and/or via lines 667 commands data signals to the control interface circuit 630–636 or 644 which the processor 324 desires to address. The control interface circuits 630–636 have no intelligence and do not on their own seek to communicate with processor 324. Instead, processor 324 just periodically writes or reads data to these control circuits.

2. Functions of Serial Communications Interface 644

The communications interface 644 has two devices connected to it which have intelligence, namely microcontroller 672 associated with the two front panels 48 and 60 on console 46 and microcontroller 674 associated with optional remote controller 370. Serial communications interface 644 converses with the microcontrollers 672 and 674 using the well-known RS-422 communications protocol at a suitable data rate, such as 9600 baud. Whenever either of these two microcontrollers has information to be sent to processor 324, it serially sends a byte of information to the communications interface 644 which in turn automatically causes an interrupt to be generated. Communications interface 644 is identified as the source of the interrupt, the interrupt is acknowledged via line 376, and the processor 324 causes data serially communicated to the DUART 647 by the microcontroller to be loaded into the data latch 630, and then via VME bus 340 reads the data from latch 630 in one of its next I/O cycles. Microcontroller 672 has its own internal oscillator and micro program. It continuously monitors all of the buttons 52 and 62 found on front panels 48 and 60 of the control console 46 to determine whether they have been depressed. The buttons are electrically arranged in a matrix of row and columns, and by interrogating each position of the matrix the state of all the buttons is determined. The microcontroller advises the processor whenever a button is pressed, and keeps periodically advising the processor 324 of this fact for as long as the button remains pressed. Microcontroller 672 also monitors, as part of the aforementioned matrix of buttons, the status of top buttons 270 and 272 and side pedals switches 278 and 280 within the footpedal assembly.

The microcontrollers 672 and 674 are provided in order to ensure that the main processor 324 is apprised of changes in status at the front panel console or remote control console virtually immediately for a very quick response to operator requests. In other words, all the routine functions which need not be performed quickly by the main processor 324 are made to wait while processor 324 responds to an interrupt and reads the data from the microcontroller and puts it into a table in main memory 325 one byte at a time. In main memory, a table listing the states of all the buttons on the main console and the remote control console is kept. The microcontrollers 672 and 674 only advise the main processor 324 of changes in the state of any of the buttons. In this manner, communications between the microcontrollers 672 and 674 are handled far more efficiently than updating the entire table each time an interrupt is generated.

Microcontroller 674 operates in the same manner as microcontroller with respect to the matrix of buttons it monitors. The remote control console 370 also contains a keyboard interface circuit almost identical to interface circuit 680. This interface circuit is described in detail in aforementioned U.S. patent application Ser. No. 427,614, filed Oct. 27, 1989, entitled "Remote Control Console For Surgical Control System."

Communications interface 644 also reads and writes data to EEPROM 646 in conventional fashion. EEPROM 646 is provided so console 46 can store, in a non-volatile manner, any user-programmed default values, configuration codes, calibration data and/or any other pertinent parameters which may be entered in by the user.

3. Accessory Control Circuit 630

The accessory control 630 contains: a plurality of memory latches and indicator light driver circuits dedicated to driving the indicator lights 620 on connector panel 90 and secondary panel 60., a plurality of memory latches, relay driver circuits, sensing circuits and an optical position decoder, all of which are dedicated to sending control signals to and receiving information from motorized IV pole hardware 368; and a latch and relay driver for operating relay 372. When a relay driving signal is applied to line 652, relay coil 372 is energized, which closes a normally open contact and thus completes the circuit available on lines 664 connected to the connector receptacle 194 shown in FIG. 1B. The details of the electrical devices and circuits in the motorized IV pole 368 are described in U.S. patent application Ser. No. 428,166, filed Oct. 27, 1989, entitled "Motorized IV Pole Assembly," and thus need not be described here.

4. Audio Control Circuit 634

The audio control circuit 634 is of standard design, and uses a conventional programmable sound generation circuit on a large scale integration (LSI) chip to produce the various tones at various amplitudes used to indicate device operation and provide audio error signals to the console user. The output signal from this chip drives a separate conventional low-power audio amplifier chip, whose output is connected to and drives speaker 366. A suitable sound generator is available from Microchip Technology, Inc. of Chandler, Ariz. as Model No. AY8930. One of the unique features provided by control console 46 is the user of select various tones and amplitudes for the selected tones to represent different conditions or states that the control system 40 may be placed in by the surgeon. A further description of this aspect of the control system 40 is provided in aforementioned U.S. patent application Ser. No. 428,232, filed Oct. 27, 1989, entitled "Control System For Opthalmic Surgical Instruments."

Footpedal Control Circuits 636-640

In accordance with commands from footpedal control 636, the detent control 638 provides positive and negative 24 volt DC power signals on lines 668 to operate the detent solenoid 296. A momentary −24 VDC signal extends the armature of solenoid 296 while a momentary −24 VDC signal causes it to retract. Conventional magnetic and/or mechanical detents built into solenoid 296 hold its armature in the last position the signals on lines 668 placed it in.

Footpedal decoder 640 receives low-voltage quadrature signals over conductors 680 from encoder 288, and a low-voltage digital signal on line 682 from zero switch 290. Switch 290 is released whenever footpedal 250 is moved more than two degrees from its spring-returned position, that is, the position pedal 250 is in when it is not pressed at all. When the signal on line 682 is in its reset state, bi-directional multiple stage digital counter 684 within decoder circuit 640 is held in a reset state. As soon as signal 682 goes to its opposite state, counter 684 is allowed to operate under the control of the quadrature signals on lines 680 which increment or decrement the counter with each pulse. Thus the accumulated count in counter 684 reflects the true angular position of footpedal 250. Processor 324 periodically (once every 50 milliseconds) reads the value in counter 684 by sending appropriate control signals to bus interface 390f so that counter 684 can send its present count to data bus 666, where it is held by latch 630 until read by the processor 324 via VME bus 340.

The status of top button switches 270 and 272 and the side pedal proximity switches 278 and 280 of the footpedal assembly 240 are also read through microcontroller 672, which as previously explained serially transmits information to communications interface 644, through internal bus 666, bus interface 390f and VME bus 340 to processor 324.

V. Mechanical Operation of the Footswitch Assembly

Referring now to FIGS. 5-13, further details of the footswitch assembly 240, described above in connection with FIG. 3, will now be discussed. As shown in FIG. 5, the footswitch assembly 240 includes switch function legends 712 and 714 which are shown in more detail in FIGS. 6 and 7. Switch legends 712 and 714 indicate schematically the various functions associated with the left and right top footswitch assemblies 262 and 264, the side pedals 258 and 260, and the footpedal 250. Functions used in the anterior mode are illustrated in FIG. 6 and functions used in the posterior mode are illustrated in FIG. 7.

Figure 10:
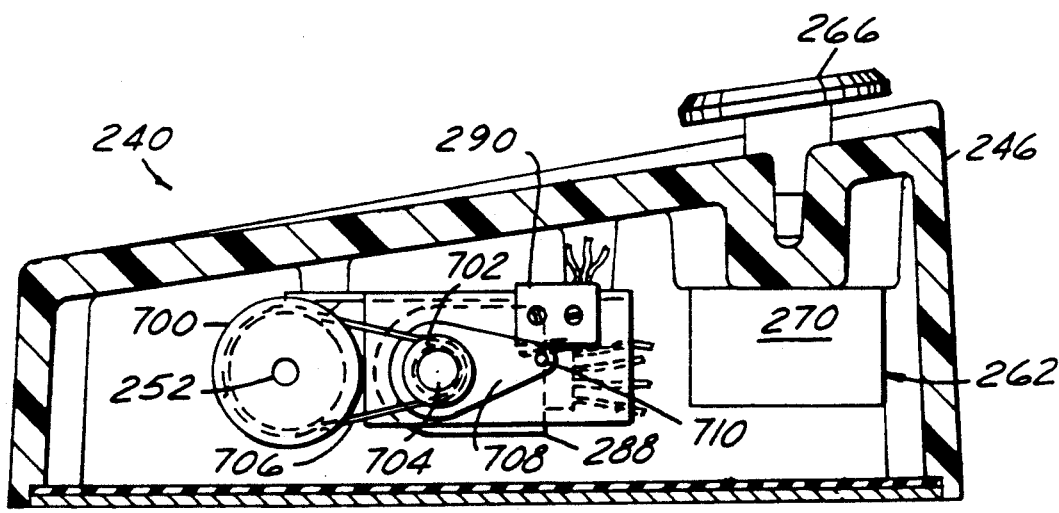
FIG. 10 is a cross-sectional side view of the footswitch assembly taken along line 10—10 in FIG. 9.
Figure 9:
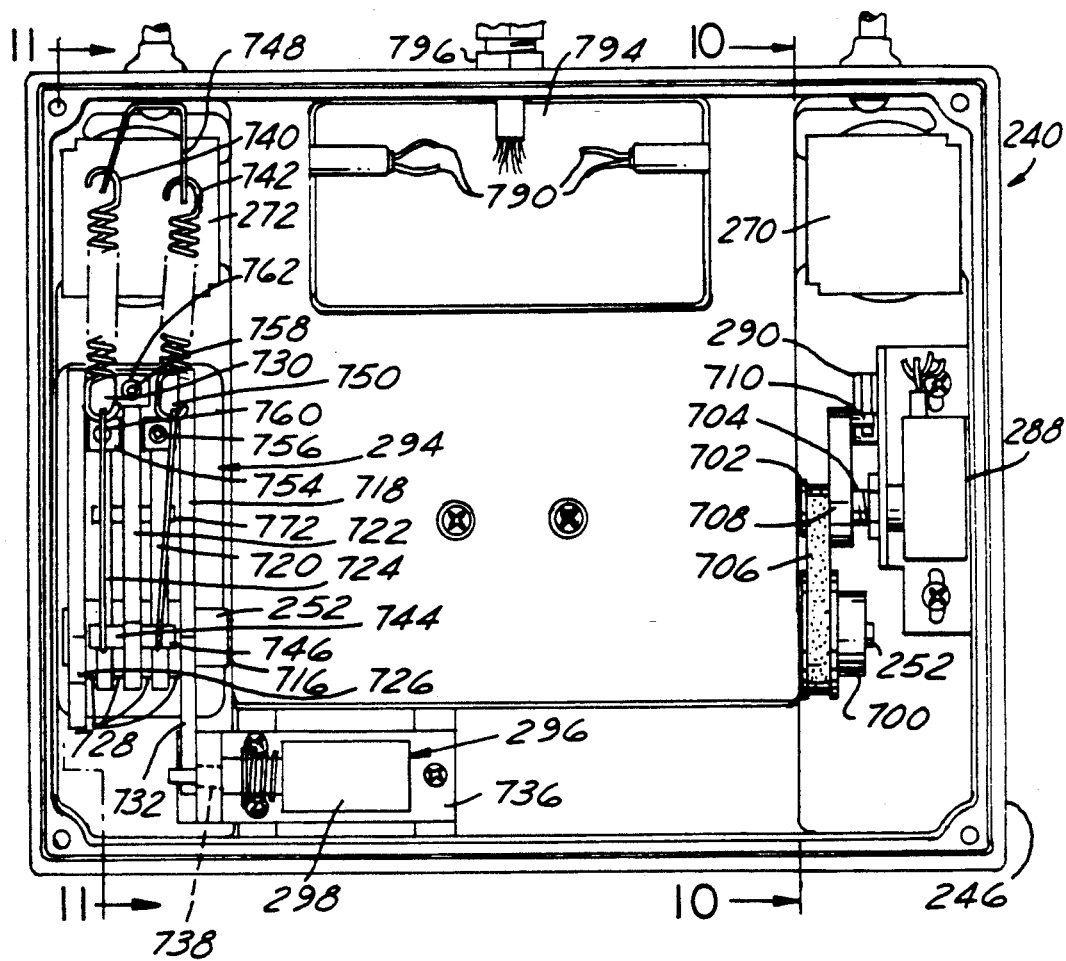
FIG. 9 is a bottom view of the footswitch assembly shown in FIG. 8.

As shown in FIG. 9-10 rotation of footpedal shaft 252 is coupled to the encoder 288 by means of a 48 tooth timing belt pulley 700 attached to the footpedal shaft 252, and an 18 tooth timing belt pulley 702 attached to an encoder shaft 704. The 48 tooth timing belt pulley 700 and the 18 tooth timing belt pulley 702 are coupled with a Kevlar reinforced neoprene timing belt 706. The two timing belt pulleys 700 and 702 have side faces to ensure that the timing belt remains in place. Zero reset switch 290 is engaged by an eccentric lobe 708, best seen in FIG. 10, attached to the encoder shaft 704 by means of two set screws. A pin 710 extends at right angles from the end of the eccentric lobe 708 to contact the reset switch 290. When footpedal 250 is pressed and footpedal shaft 252 rotates approximately two degrees, eccentric lobe 708 will move sufficiently to release zero reset switch 290, and encoder 288 will begin to count. When footpedal is released, zero reset switch 290 will be depressed again by lobe 708 and the encoder 288 count is reset to zero. Zero reset switch 290 is a normally closed contact so that it does not close until the eccentric lobe 708 comes off the switch 290 upon pressing of the footpedal. The encoder 288 is made by Hewlett-Packard which is used with a 4× decoding chip which yields 2,048 counts per revolution. Approximately 60 degrees of encoder travel is used, giving approximately 320 pulses over the full travel of the footpedal 250. The software actually only uses about 300 pulses. There is approximately an equal amount of dead band on either side of the 300 pulses for over travel purposes. This helps ensure accurate readings, by ensuring that neither the footpedal 250 nor the encoder 288 are at the limit of their travel.

The full range of travel of the footpedal 250 is on the order of 20 degrees to 22 degrees. This is translated to approximately 60 degree travel on the encoder shaft 74 by means of the 48 tooth gear 700 and the 18 tooth gear 702 as described above.

Referring again to FIG. 9, it is shown that footpedal shaft 252 is attached to spring detent shaft 716 by means of a roll pin (not shown) passed through a hole drilled into the near end of the detent shaft 716. Detent shaft 716 is preferably a solid carbon-steel rod. The spring-detent assembly 294 includes five detent plates including a first, second, third, fourth and fifth detent plate, 718, 720, 722, 724, and 726 respectively. The five detent plates 718-726 are spaced parallel to one another axially along the detent shaft 716. The central, or third, plate 722 is welded to the detent shaft 716, while the other four detent plates are free to rotate upon ball bearings (not shown). Four nylon spacers 728 are used to ensure proper separation between the detent plates 718-726. The ball bearings are pressed into place on the detent plates and have a slip fit on the shaft 716. The reason the overall collection of detent plates 718-726 remain in place on this shaft 716 is that the center detent plate 722 is welded to the shaft and the two outer detent plates 718 and 726 are connected to one another by a connecting bar/adjustment block 730 which is located at the outer end of the detent plates 718 and 726 remote from the detent shafts 716. Thus, the four nylon spacers 728 and four outer detent plates 718, 720, 724 and 726 cannot move axially along shaft 716 relative to the welded center detent plate 722.

Figure 11:
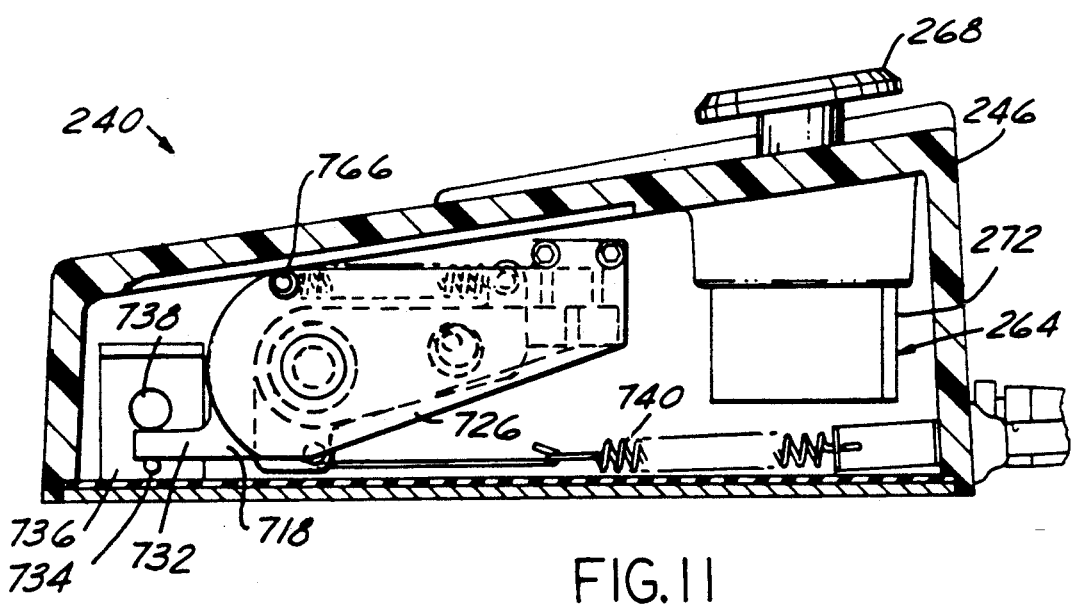
FIG. 11 is a cross-sectional Side view of the left side of the footswitch assembly taken along line 11—11 in FIG. 9.

Solenoid assembly 296 engages with outer detent plate 718 as follows. Detent plate 718 has a stop lever 732 extending outwardly therefrom, which contacts a roll pin 734 extending from a solenoid frame 736. Since the pin 734 and solenoid frame 736 are stationary with respect to the housing 246, the point at which stop lever 732 contacts pin 734 will determine the full-up stop position of the detent assembly 294. Solenoid assembly 296 includes a solenoid shaft 738 which reciprocates through an opening in the solenoid frame 736 when the solenoid is energized to its extended position. As seen in FIG. 11, when solenoid shaft 738 is in the extended position, stop lever 732 of the first detent plate 718 is captured between the roll pin 734 and the solenoid shaft 738.

Figure 13A:
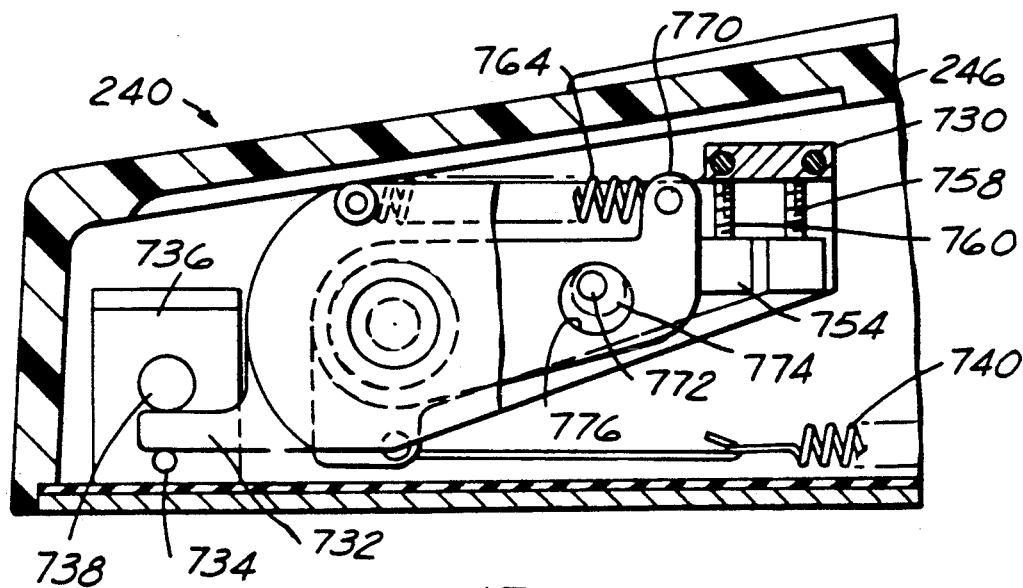
FIG. 13A and B are side views partially in cross-section of the spring detent assembly in upward and downward footpedal positions in a second mode of operation of the footswitch assembly shown in FIG. 9.
Figure 13B:
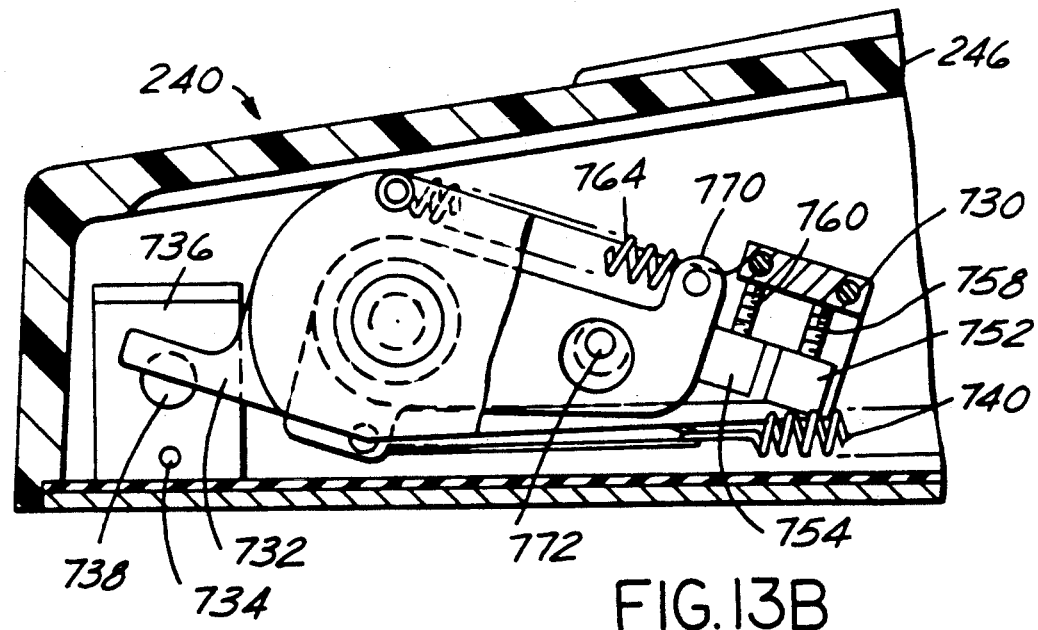

When the solenoid shaft 738 is in the retracted position, the detent assemblies 294 has only one spring rate, called the first spring rate. The first spring rate is determined by two parallel extending springs 740 and 742 connected to pins 744 and 746 extending perpendicularly from either side of the center detent plate 722. The other end of springs 740 and 742 are fastened to a spring bracket 748 which is fastened to the footswitch housing 246. FIG. 13A shows the detent assembly 294 in the pedal-up position, while FIG. 13B shows the pedal-down position, both with the detent 738 retracted.

When solenoid shaft 738 is in a retracted position, all five plates 718-726 move together synchronously when footpedal 250 is pressed. Thus the only resistance is by springs 740 and 742. Springs 740 and 742 are selected to achieve approximately a six pound force upon full depression of the footswitch pedal 250.

To achieve multiple spring rate throughout the travel of footpedal 250 with detent 738 in the extended position, the following structure is employed. On the end of the second 720, third 722 and fourth 724 detent plates are blocks 750, 752 and 754 respectively, having a threaded hole through which threaded adjustment screws 756, 758 and 760, are run. These adjustment screws 756-760 are turned with an allen wrench, but other conventional mechanisms may be used if desired. The center plate adjustment screw 758 is used to adjust the pedal height in the at-rest position, which effectively determines the total number of counts from the encoder 286 through the full length of footswitch travel. This is factory set in order to have a uniform number of counts with each footswitch assembly 240 manufactured.

The second 720 and fourth 724 detent plates are used in conjunction with second and third rate springs 762 and 764 respectively. The adjustment screws 756 and 760 associated with the second 720 and fourth 724 detent plates determines the point at which additional spring load connected to its detent plates becomes operational when the footswitch is in the detent mode. Springs 762 and 764 are connected to a spring shaft 766 which extends perpendicularly to the outer detent plates 718 and 726. Thus the spring shaft 766 and the adjustment block 730 extending between the outer detent plates effectively cause the outer detent plates 718 and 726 to be a solid structure which rotates in unison and has a rigid frame.

Near the outer end of the second and fourth detent plates, 720 and 724, are lobes 768 and 770 having a hole therein to which the second and third rate spring 762 and 764 respectively are connected. Thus, these springs extend between the spring shaft 766 adjacent the detent shaft 738 and the lobe 768, 770 at the outer end of the detent plates 720 and 724.

The center detent plate 722 has a pin 772 extending outwardly through centrally located holes 774 and 776 in the second and fourth detent plates 720 and 724. This pin 772 in the center detent plate 722 may be called the pickup pin since as the center detent plate rotates, the pickup pin 722 contacts first the second detent plate 720 and then later the fourth detent plate 724 to kick in the second and third spring rates respectively. The size of the hole 774, in combination with the setting of the adjustment screw 756 for the second detent plate 720 determines when it kicks in. Similarly, the size of the hole 776 and the setting of the adjustment screw 760 determines when the fourth detent plate 724 kicks in. It will be appreciated that either spring 762 or 764 may be used as the second or third spring rate; however, in the preferred embodiment the second detent plate 720 is used in conjunction with the second spring 762 for the second spring rate as a matter of convention.

Figure 12A:
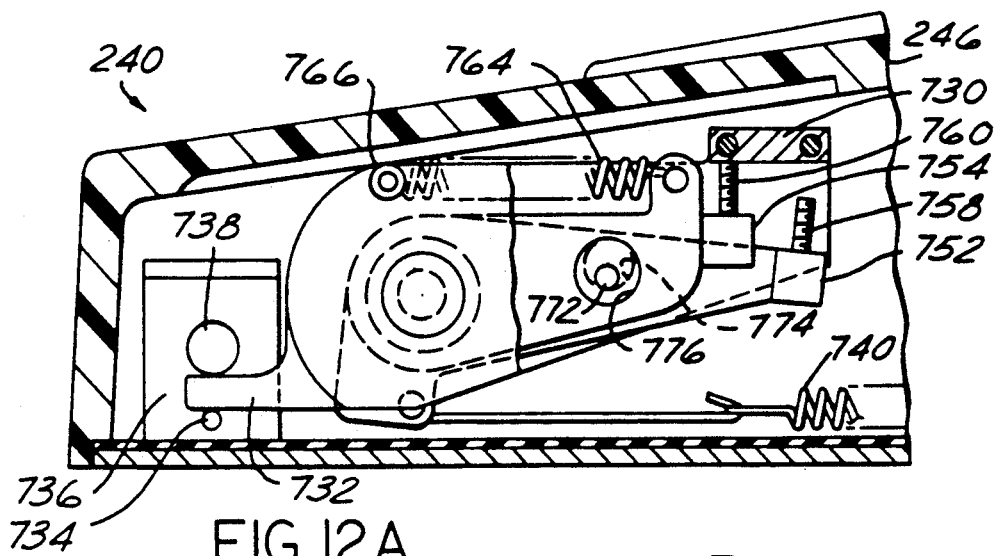
FIG. 12A-C are side views of the spring detent assembly showing three positions of the footpedal in the footswitch assembly shown in FIG. 9.
Figure 12B:
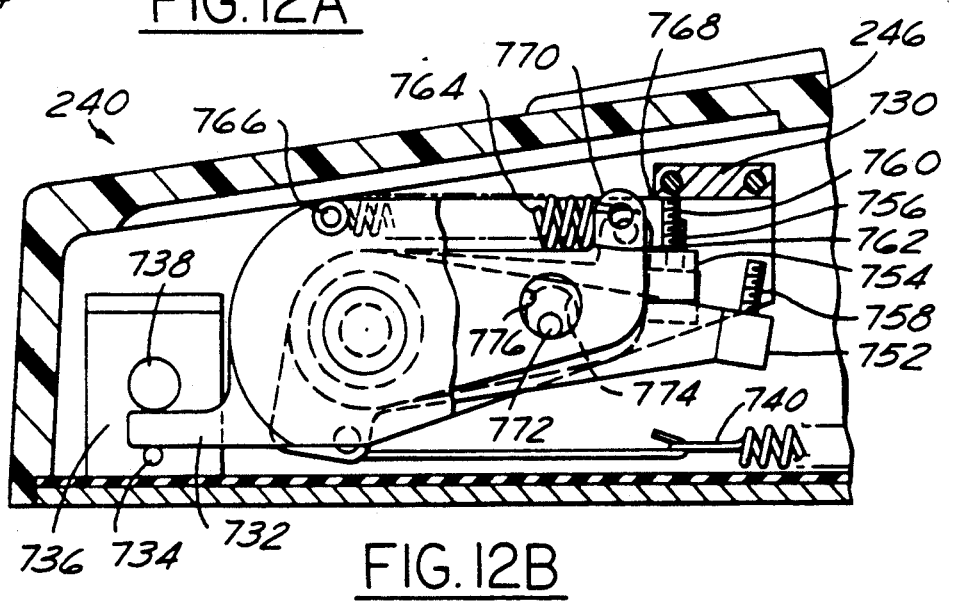
Figure 12C:
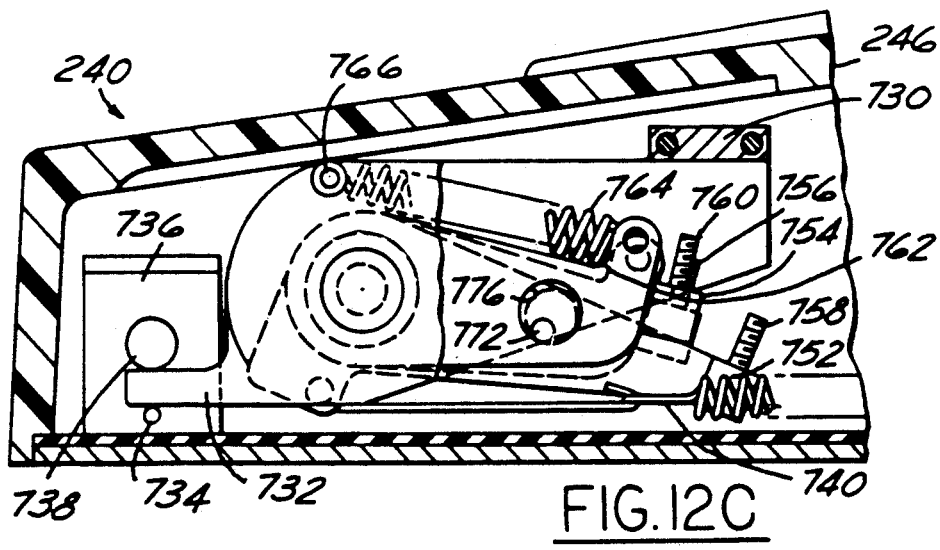

Consequently, when solenoid shaft or detent 738 is extended, as shown in FIGS. 12A-12C, the outer frame formed of the first 718 and fifth 726 detent plate, the adjustment block 730 and spring shaft 766 is now fixed and cannot rotate when the pedal shaft 252 and detent shaft 716 rotate together.

As the pedal 250 is depressed, the two shafts 252 and 716 rotate, and the center plate 722 rotates, against the first rate springs 740 and 742.

When pedal shaft 252 has rotated about 6 degrees or about 30% of the total pedal travel, the pickup pin 772 of the center detent plate 722, which also moves with the center detent plate 722, eventually contacts the bottom side of the pickup hole 774 in the second detent plate 720 as illustrated in FIG. 12A. At this point, the cumulative spring load felt by the pedal 250 will increase as determined by the sum of the resistances provided by the first rate springs 740 and 742 and the second rate spring 762 connected to the second detent plate 720 in the manner previously described.

As the footpedal 250 is pressed downward and center detent plate 722 rotates further, the pickup pin 772 eventually contacts the lower side of the pickup hole 776 in the fourth detent plate 724. This point is illustrated in FIG. 12B. The cumulative spring load now felt by the footpedal assembly 240 is determined by the first, second and third rate springs 740, 742. 762 and 764.

Figure 8:
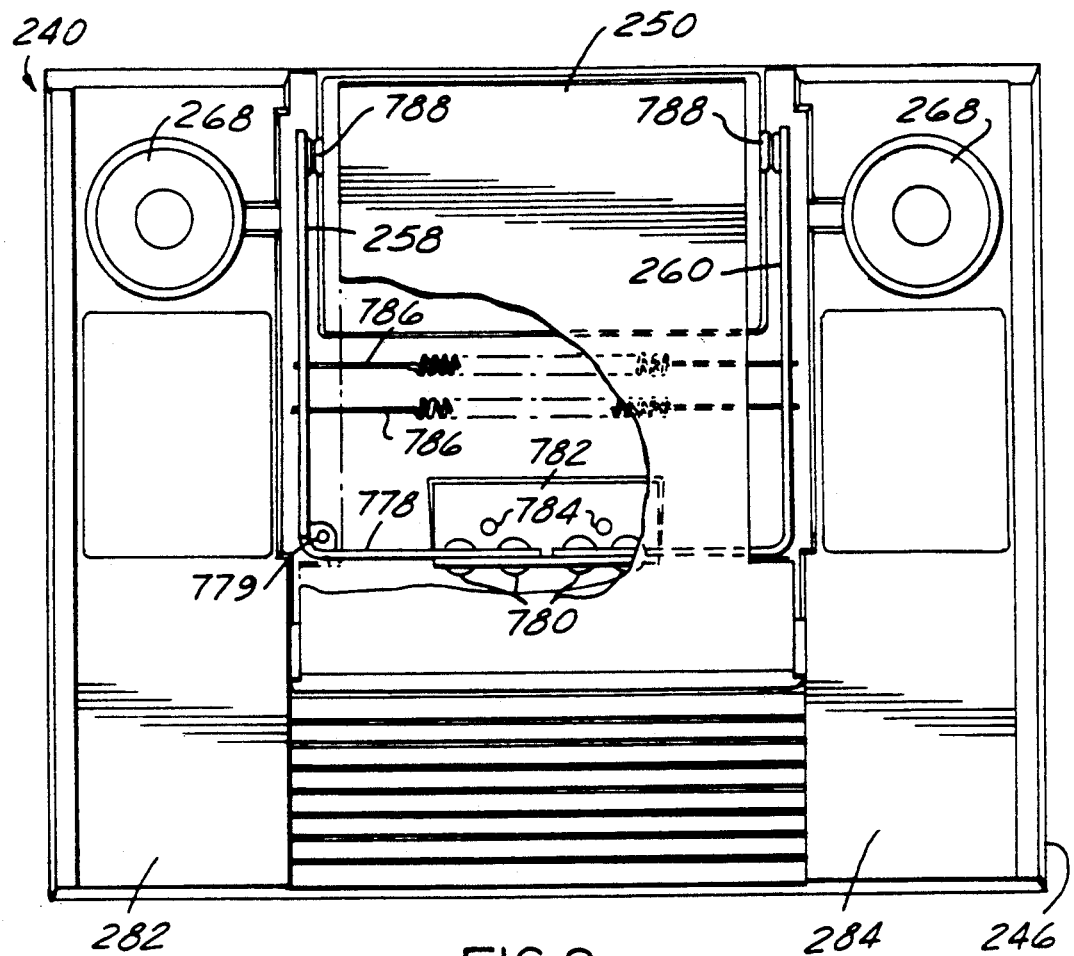
FIG. 8 is a top view of the footswitch assembly shown in FIG. 1 partially in cross-section.

Referring now to FIG. 8, the pedal assembly 240 includes sidepedals 258 and 260 located on the left and right sides of the main pedal 250. In a recess under the main pedal is a horizontal U-shaped bracket 778 which has shoulder screws 780 that are driven in by an allen wrench to the U-shaped bracket 778. The shoulder screws 780 are approximately one-quarter inch in diameter and have a three-eights inch smooth cylindrical shoulder portion, and a three-sixteenths inch threaded portion which is turned into a threaded hole in the bracket 778. The shoulder of the shoulder screw 780 holds down a hinge block 782 to which the sidepedals 258 and 260 are mounted by two machine screws 784. A return spring 786 extends between the two sidepedals 260 and 258 with a semi-circular hook at the end of the spring being passed through corresponding holes and slots in the sidepedals 258, 260. The sidepedals 258 and 260 are only used in an on-off manner. Alternatively, as shown in the left side of U-shaped bracket 778, a conventional hinge pin 779 may be used to provide hinging action. Actuations of the sidepedals 258, 260 is determined by waterproof microswitches 788, which are mounted at the upper left and right hand sides of the U-shaped bracket 778. The microswitches 788 are attached to conductors 790, seen in FIG. 9, and are potted. Conventional potting compound is used to seal the wires 790 in this opening.

In the upper center of the underside of the housing 246 as shown in FIG. 9, is located a wiring cavity 794 to which various wires are bundled and connected to a conventional cable feedthrough assembly 796. A 15-wire cable 242, shown in FIG. 3, is approximately 12 feet long and is connected to this feedthrough 796. The feedthrough 796 is also watertight. The particular connector 796 used is made by AMP and is a 14-pin connector, with the 15th wire in the cable being a spare.

The sidepedals 258, 260 are stopped from further movement by the left and right bunker structures 282 and 284 which are approximately two inches wide and nine inches long and two and one-half inches high. Near the upper corner of each bunker structure 282 and 284 are the mushroom heads 266 and 268 of the left and right top foot switch assemblies 262 and 264, as shown in FIG. 8. Foot switch assemblies 262 and 264 are conventional Furnace brand, oiltight industrial duty pushbutton switches. The top right foot switch 264 is used to turn on and off auxiliary accessories as indicated in FIGS. 6 and 7. The left foot switch assembly 262 is used to turn off and on the bipolar cautery function. As shown in FIGS. 6 and 7 these pushbutton switches 262 and 264 have the same function in both the anterior segment and posterior segment modes of operation of the console. The sidepedals 258 and 260 are used differently depending on whether in the anterior or posterior mode of operation. In the anterior mode, as shown in FIG. 6 the left sidepedal 258 is used to control reflux, while the right sidepedal is used to control the cutter space CAC (controlled anterior capsulotomy) function. In the posterior mode, as shown in FIG. 7, the left sidepedal 258 is used to turn the MICROVIT ® cutter off, while the right sidepedal is used to turn the MI- CROVIT® cutter on. In the fragmentation mode, the right sidepedal is used to turn the fragmentation on and off.

The foregoing detailed description shows that the preferred embodiments of the present invention are well-suited to fulfill the objects above stated. It is recognized that those skilled in the art may make various modifications or additions to the preferred embodiments chosen to illustrate the present invention without departing from the spirit and proper scope thereof. For example, the footswitch assembly may employ fewer or greater than three spring rates, or, a non-optical position encoder may be used. In addition, the footswitch may be used for non-ophthalmological surgical instruments. Further, the footswitch assembly may be employed for other types of nonsurgical instruments. Accordingly, it is to be understood that the protection sought and to be afforded hereby should be deemed to extend to the subject matter defined by the appended claims, including all fair equivalents thereof.

I claim:

1. A footswitch apparatus for surgical instruments comprising:
   a) a housing;
   b) a footpedal movably mounted on said housing;
   c) means for limiting the range of motion of said footpedal within first and second limits;
   d) first, second and third resilient means for resisting movement of said footpedal in one direction and for returning said footpedal to one of said limits in the other direction;
   e) said first resilient means providing a first resilient force substantially throughout the range of motion of said footpedal;
   f) said second resilient means providing a second resilient force in a first zone of travel of said footpedal within said range of motion;
   g) said third resilient means providing a third resilient force in a second zone of travel of said footpedal within said range of motion; and
   h) means for selectively disengaging said second and third resilient means so that only the force from said first resilient means is provided throughout said range of motion.

2. The footswitch apparatus as set forth in claim 1 wherein said means for selectively disengaging said second and third resilient means comprises a solenoid.

3. The footswitch apparatus as set forth in claim 1 further comprising means responsive to the movement of said footpedal for altering the operation of a surgical instrument when said footpedal travels from one of said zones of travel to the other.

4. The footswitch apparatus as set forth in claim 1 wherein said first resilient means comprises a first movable actuating member and a first spring means coupled to said footpedal throughout said range of motion, said second resilient means comprises a second movable actuating member and second spring means coupled to said footpedal throughout said first zone of travel, and said third resilient means comprises a third movable actuating member and a third spring means coupled to said footpedal through said second zone of travel.

5. The footswitch apparatus as set forth in claim 3 wherein said means responsive to the movement of said footpedal further comprises a position encoder means for detecting the position of said footpedal and transmitting a signal to said instrument in response to said detected position.

6. The footswitch apparatus as set forth in claim 1 further comprising at least one side actuator means mounted on said housing adjacent said footpedal for providing further control over said instrument.

7. The footswitch apparatus as set forth in claim 1 further comprising at least one on/off switch means mounted on said housing for providing further control over said instrument.

8. A footswitch apparatus for surgical instruments comprising:
   a) a housing;
   b) a footpedal movably mounted on said housing;
   c) means for limiting the range of motion of said footpedal within first and second limits;
   d) first and second resilient means for resisting movement of said footpedal in one direction and for returning said footpedal to one of said limits in the other direction;
   e) said first resilient means providing a first resilient force substantially throughout the range of motion of said football;
   f) said second resilient means providing a second resilient force in a zone of travel of said footpedal within said range of motion; and
   g) means for selectively disengaging said second resilient means so that only the force from said first resilient means is provided throughout said range of motion.

9. In a footswitch apparatus for enabling remote control operation of a surgical instrument by an operator, said apparatus comprising:
   a) a housing
   b) a footpedal movably mounted to said housing for movement throughout multiple zones of travel within a range of motion;
   c) a plurality of spring means coupled to said footpedal for providing different spring rates in selected ones of said zones of travel;
   d) means for transmitting signals for altering the operation of said instrument in response to the movement of said footpedal from one zero of travel to another, said operator being given continuous tactile feedback as to which zone of travel the footpedal is in; and
   e) means for selectively decoupling all but one of said spring means in order to provide a single spring rate throughout the range of motion of said footpedal.

10. The footswitch apparatus as set forth in claim 9 wherein said means for selectively decoupling comprises a solenoid.

11. The footswitch apparatus as set forth in claim 9 further comprising a plurality of movable actuating members each attached to one of said spring means and coupled to the motion of said footpedal throughout said selected zone of travel for each spring means.

12. The footswitch apparatus as set forth in claim 9 wherein said means for altering the operation of said surgical instrument further comprises a position encoder means for detecting the position of said footpedal and transmitting a signal to said instrument in response to said detected position.

13. The footswitch apparatus as set forth in claim 9 wherein said surgical instrument operates in different modes when said footpedal is in corresponding different zones of travel.

14. The footswitch apparatus as set forth in claim 9 further comprising at least one side actuator means mounted on said housing adjacent said footpedal for providing further control over said instrument.

15. A footswitch apparatus for enabling remote control operation by an operator of a surgical instrument through a controller unit, said footswitch apparatus comprising:

a) a housing;

b) a footpedal movably mounted on said housing for movement throughout multiple zones of travel within a range of motion;

c) at least one side actuator means mounted on said housing adjacent said footpedal and coupled to said controller unit for providing further control over said surgical instrument;

d) first movable actuating means coupled to the motion of said footpedal throughout the range of motion of said footpedal;

e) first spring means attached to said first actuating means and also to said housing for resisting the motion of said first actuating means;

f) second actuating means coupled to the motion of said footpedal throughout two of said multiple zones of travel;

g) second spring means attached to said second actuating means and also attached to said housing for resisting the motion of said second actuating means throughout said two zones of travel of said footpedal;

h) third actuating means coupled to the motion of said footpedal throughout one of said zones of travel;

i) third spring means attached to said third actuating means and also attached to said housing for resisting the motion of said third actuating means throughout said one of said zones of travel;

j) an optical position encoder means for detecting the position of said footpedal from one of said zones of travel to another, whereby said operator is given continuous tactile feedback as to which zone of travel the footpedal is in; and k) means for selectively decoupling all but one of said spring means from said footpedal for providing a single spring rate throughout the range of motion of said footpedal.

* * * * *

UNITED STATES PATENT AND TRADEMARK OFFICE
CERTIFICATE OF CORRECTION

PATENT NO. : 5,091,656

DATED : February 25, 1992

INVENTOR(S) : Gerald S. Gahn

It is certified that error appears in the above-identified patent and that said Letters Patent is hereby corrected as shown below:

Column 1, line 40;    change "andophthalmic" to --and ophthalmic--.

Column 14, line 50;   before "Footpedal" add --5.--.

Column 20, line 41;   after "one" change "zero" to --zone--.

Signed and Sealed this

Twenty-ninth Day of June, 1993

Attest:

MICHAEL K. KIRK

Attesting Officer

Acting Commissioner of Patents and Trademarks